(12) United States Patent  (10) Patent No.: US 8,376,949 B2
Sasaki et al.  (45) Date of Patent: Feb. 19, 2013

(54) ULTRASONIC DIAGNOSTIC APPARATUS AND METHOD OF CONTROLLING THE SAME

(75) Inventors: Takuya Sasaki, Tochigi-Ken (JP); Akihiro Kakee, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 1047 days.

(21) Appl. No.: 12/331,630

(22) Filed: Dec. 10, 2008

(65) Prior Publication Data
US 2009/0156937 A1  Jun. 18, 2009

(30) Foreign Application Priority Data

Dec. 12, 2007 (JP) ................. P2007-321192

(51) Int. Cl.
*A61B 8/00* (2006.01)
(52) U.S. Cl. ...................... 600/443; 600/437
(58) Field of Classification Search .............. 600/437, 600/443, 450
See application file for complete search history.

(56) References Cited

U.S. PATENT DOCUMENTS 6,544,175 B1 4/2003 Newman
7,288,068 B2 * 10/2007 Bakircioglu et al. ......... 600/455

FOREIGN PATENT DOCUMENTS

JP    2007-20908    2/2007

* cited by examiner

*Primary Examiner* — Peter Luong
(74) *Attorney, Agent, or Firm* — Oblon, Spivak, McClelland, Maier & Neustadt, L.L.P.

(57) ABSTRACT

In an ultrasonic diagnostic apparatus, a scan controller inputs a trigger signal corresponding to heartbeat period, scans an ultrasonic beam such that a particular diagnostic region of a body under examination is scanned with the ultrasonic beam a plurality of times in response to each trigger signal, and controls the scan repetition period by controlling the pulse repetition period of the transmission pulse. An image generation unit generates an image corresponding to each of the pulse repetition periods. The scan controller controls the pulse repletion period such that an integral multiple of the scan repetition period is equal to a reference value determined based on the period of the trigger signal.

16 Claims, 14 Drawing Sheets

ULTRASONIC DIAGNOSTIC APPARATUS AND METHOD OF CONTROLLING THE SAME

BACKGROUND OF THE INVENTION

1. Field of the Invention

The present invention relates to an ultrasonic diagnostic apparatus and a control method thereof, and more particularly, to an ultrasonic diagnostic apparatus configured to three-dimensionally scan the inside of a body under examination using an ultrasonic wave in response to a trigger signal generated based on an electrocardiogram signal or the like, and a method of controlling such an ultrasonic diagnostic apparatus.

2. Description of the Related Art

In recent years, an ultrasonic diagnostic apparatus capable of displaying a three-dimensional moving image has been in active development, and it has become possible to display a three-dimensional diagnostic image with higher resolution over a larger region than in conventional two-dimensional images.

The ultrasonic diagnostic apparatus generates a diagnosis image using an ultrasonic wave propagating in a living body, and thus the time from the transmission of an ultrasonic pulse to the reception of a reflected wave from a living body is basically the same for a three-dimensional ultrasonic diagnostic apparatus and a two-dimensional ultrasonic diagnostic apparatus. To scan a three-dimensional region in a living body with high resolution, a great number of scanning beam positions are required. Thus, the three-dimensional ultrasonic diagnostic apparatus generally needs a longer time to scan a specified region than the two-dimensional ultrasonic diagnostic apparatus needs. In other words, when the spatial resolution is equal, the frame rate of the three-dimensional image (i.e., the frequency at which the three-dimensional image is updated) obtained by the three-dimensional ultrasonic diagnostic apparatus is theoretically lower than the frame rate of the two-dimensional image obtained by the two-dimensional ultrasonic diagnostic apparatus.

To solve the problem described above, various techniques have been proposed (see, for example, U.S. Pat. No. 6,544,175, JP-A 2007-20908, etc.). A basic idea of these techniques is to divide a full region (volume) under examination for diagnosis (hereinafter, referred to simply as a full volume) into a plurality of small regions (hereinafter referred to as sub volumes), and obtain a three-dimensional image of the full volume by connecting image data obtained by scanning three-dimensional space of the sub volumes at a high frame rate. In this technique, the observation time of sub volumes varies from one to another. Therefore, it is important to connect sub volumes so that good spatial continuity is achieved.

Depending on a part under diagnosis, the part can move due to breathing or a heartbeat. To avoid a problem due to the motion of the part under diagnosis, for example, U.S. Pat. No. 6,544,175 discloses a technique to acquire a plurality of image data in a sub volume in synchronization with the motion of a heart. In this technique disclosed in U.S. Pat. No. 6,544,175, a three-dimensional moving image of a heart is produced in real time as described briefly below.

In this technique, a signal of an electrocardiogram, i.e., an ECG signal is used as a signal synchronous with motion of a heart. More specifically, an R-wave signal, which appears at the end of a diastolic period, is used as an ECG trigger signal.

A three-dimensional full volume of a heart under examination is divided into, for example, four sub volumes, and image data of one heartbeat is captured in synchronization with the ECG trigger signal for each sub volume. Note that the image data of one heartbeat includes a plurality of frames of images. For example, 20 frames of images of one sub volume are obtained by repeatedly scanning the sub volume 20 times for one heartbeat (during one interval of the ECG trigger signal). In this case, if the repetition period of the heartbeat is assumed to be one second, the image data of each sub volume is obtained at a frame rate of 20 fps, which is reasonably high to obtain a moving image representing motion of a heart.

The plurality of frames of image data obtained for each sub volume are connected to obtain a full volume of image data as follows. That is, frame images that are same in "time phase" are extracted from the plurality of fame images of sub volumes and are connected together so as to obtain a frame image of the full volume. The "time phase" refers to a delay with respect to a time at which an ECG trigger signal is generated. The motion associated with contraction and relaxation of the heart normally has periodicity synchronous with the ECG trigger signal. Therefore, by extracting frame images which are equal in the time phase from the respective sub volumes and connecting the extracted frame images, it is possible to obtain good spatial continuity between the sub volumes. In practice, successive "time phase numbers" are assigned to frame images in scanning order from one closest to an ECG trigger signal, and an image of a full volume is synthesized by connecting frame images having an equal time phase number. For example, in a case where the full volume is divided into four sub volumes A, B, C, and D and each sub volume is scanned repeatedly 20 times, a total of twenty frame images with time phase numbers of 0 to 19 are obtained for each sub volume. Frame images with each equal time phase number are extracted from the sub volumes A, B, C, and D and the extracted frame images are connected together thereby obtaining a synthesized image of the full volume corresponding to the time phase number. The combining of frame images is performed for each of the time phase numbers so as to obtain synthesized full volume images with time phase numbers from 0 to 19. Thus, a total of twenty synthesized full volume frame images are obtained for each ECG trigger signal. Note that the frame rate of the full volume images is equal to that of the sub volume images. Thus, for example, a full volume moving image with a frame rate of 20 fps is obtained.

As described above, in the conventional technique disclosed in U.S. Pat. No. 6,544,175, each sub volume is scanned a plurality of times in response to each ECG trigger signal. In the repeatedly performed scanning operation described above, in general, the sub volumes are scanned while changing the transmission direction of the ultrasonic beam from one transmission pulse to another. Thus, in general, the time needed for each scanning (hereafter, referred to as a scan repetition period (the reciprocal thereof corresponds to the frame rate of the sub volumes)) is determined by the product of the pulse repetition period of the transmission pulse and the number of beam positions of the transmission ultrasonic beam.

Of these parameters, the pulse repetition period is limited by the maximum diagnosis distance of a part to be examined (the depth of the part to be examined). If the pulse repetition period is too short, the maximum detectable depth becomes small. Conversely, if the pulse repetition period is too long, the scan repetition period of each sub volume becomes long and the frame rate decreases, which results in a reduction in time resolution of the moving image.

In view of the above, in general, the pulse repetition period is set to a constant value that allows the frame rate to become as high as possible within a range that allows the required maximum diagnostic distance to be achieved, and the transmission beam position is changed every pulse repetition period set to the constant value.

On the other hand, the number of transmission beam positions in the sub volume is determined by the area size of the sub volume, i.e., the scanning range of the sub volume. When the number of sub volumes into which the full volume is divided is constant, the area size of one sub volume is determined by the area size of the full volume and thus the number of transmission beam positions is determined by the area size of the full volume, which is nearly equal to the area size of the part to be examined for diagnosis.

The pulse repetition period and the number of transmission beam positions are determined by the depth and the area size of the part to be examined for diagnosis in the above-described manner, and thus the repletion scanning period is determined. Therefore, when the depth and the area size of the part to be examined are fixed, the scan repetition period is allowed to be set to a constant value. Thus, in the conventional technique, the scan repetition period is set to a constant value.

Incidentally, as described above, the repetitive scanning operation of one sub volume is started in response to an ECG trigger signal, and the same sub volume is scanned repeatedly until a next ECG trigger signal comes. If the next ECG trigger signal comes, the repetitive scanning operation on a next adjacent sub volume is started, and this sub volume is scanned repeatedly.

Therefore, if the interval of the ECG trigger signal, i.e., the heartbeat period is not equal to an integral multiple of the predetermined constant scan repetition period, the scanning operation in a period immediately before the arrival of an ECG trigger signal is aborted before the scanning in that period is completed. As a result, the image acquired in this repetition period is incomplete and useless, and thus the obtained image is discarded without being used. This causes a reduction in the efficiency of using the acquired data. Besides, it becomes impossible to obtain a heart image in the state immediately before the ECG trigger signal.

The above mentioned problems arise not only for the case where the full volume is divided into the sub volumes but also for the case where the full volume is scanned without division into the sub volumes, so long as the ECG trigger signal is used for a starting signal of the scanning of the sub volume or the full volume.

Thus it is desirable to provide an improved technique to solve the above problem in diagnosis.

SUMMARY OF THE INVENTION

In view of the above, it is an object of the present invention to provide an ultrasonic diagnostic apparatus capable of acquiring whole image data including image data immediately before an ECG trigger signal without having an interrupt in the middle of a scanning operation immediately before the ECG trigger signal thereby allowing the acquired data to be used in a highly efficient manner, and a method of controlling such an ultrasonic diagnostic apparatus.

In an aspect of the present invention, there is provided an ultrasonic diagnostic apparatus including an ultrasonic probe configured to output a transmission pulse while scanning an ultrasonic beam in a main scanning direction and a sub scanning direction and detect a reflection signal from the inside of a body under examination, a scan controller configured to input a trigger signal output every heartbeat period from the outside, scan the ultrasonic beam such that a particular diagnostic region of the body under examination is scanned with the ultrasonic beam a plurality of times for a period from one trigger signal to a next trigger signal, and control the scan repetition period by controlling the pulse repetition period of the transmission pulse, and an image generation unit configured to generate an image corresponding to each of the scan repetition periods, the scan controller being configured to determine the pulse repletion period such that an integral multiple of the scan repetition period is equal to a reference value determined based on the period of the trigger signal, and control the pulse repletion period according to the determination.

In an aspect of the present invention, there is provided a method of controlling an ultrasonic diagnostic apparatus, including the steps of (a) outputting a transmission pulse while scanning an ultrasonic beam in a main scanning direction and a sub scanning direction and detecting a reflection signal from the inside of a body under examination, (b) inputting a trigger signal output every heartbeat period from the outside, scanning the ultrasonic beam such that a particular diagnostic region of the body under examination is scanned with the ultrasonic beam a plurality of times for a period from one trigger signal to a next trigger signal, and controlling the scan repetition period by controlling the pulse repetition period of the transmission pulse, and (c) generating an image corresponding to each of the scan repetition periods, wherein in the step (b), the pulse repletion period is determined such that an integral multiple of the scan repetition period is equal to a reference value determined based on the period of the trigger signal, and the pulse repletion period is controlled according to the determination.

DESCRIPTION OF THE EMBODIMENTS

Embodiments of an ultrasonic diagnostic apparatus and a control method thereof according to the present invention are described below with reference to the accompanying drawings.

(1) General Configuration

Figure 1:
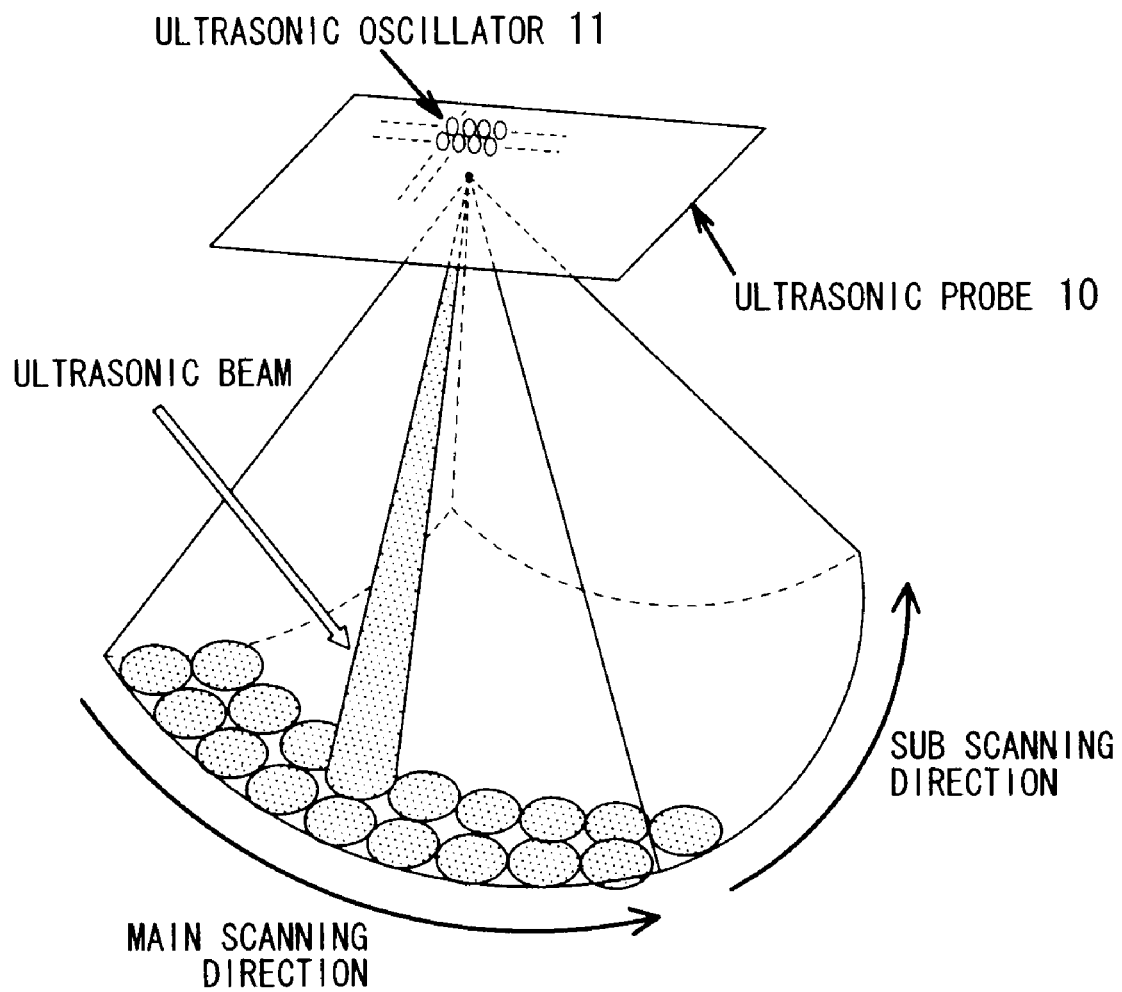
FIG. 1 is a diagram schematically illustrating a beam scanning operation of a three-dimensional ultrasonic diagnostic apparatus.

FIG. 1 is a diagram schematically illustrating an ultrasonic beam scanning operation of an ultrasonic diagnostic apparatus 1 according to an embodiment of the present invention. The ultrasonic diagnostic apparatus 1 generates a fine ultrasonic beam using an ultrasonic probe 10 including a two-dimensional array of ultrasonic oscillators 11. The generated ultrasonic beam is directed to a target part of a body under examination while being electrically deflected so that the part under examination is scanned by the ultrasonic beam in a main scanning direction and a sub scanning direction. From a reflection signal from the part under examination, three-dimensional information in terms of the main scanning direction, the sub scanning direction, and the distance is obtained.

In a conventional one-dimensional ultrasonic probe, ultrasonic oscillators are arranged in the form of a one-dimensional array and scanning is performed in a two-dimensional range, i.e. a plane. In contrast, in the two-dimensional ultrasonic probe 10 according to the present embodiment of the invention, scanning is performed in a three-dimensional range, i.e. a volume. Furthermore, because the ultrasonic beam used in the scanning has a small beam width, it is possible to obtain three-dimensional information with high resolution over a large region. From the obtained three-dimensional information, it is possible to produce a three-dimensional image viewed from an arbitrary direction or an image of an arbitrary cross section thereof.

However, because the ultrasonic beam is scanned in both directions, i.e., in the main scanning direction and the sub scanning direction, the number of beam positions in the whole region under examination (the full volume) is much greater than that in the case in which the beam is scanned in a plane. Therefore, if the scanning is simply performed sequentially from a start point to an end point in the full volume, it takes a long time to completely scan the full volume, and thus the frame rate of the image of the full volume becomes low.

In the ultrasonic diagnostic apparatus 1 according to the present embodiment of the invention, to solve the above problem, as described above, the full volume is divided into a plurality of sub volumes (four sub volumes, for example) and each sub volume is scanned at a high frame rate (20 fps, for example). Frame images obtained for the respective sub volumes are connected so as to obtain a synthesized frame image of the full volume. The resultant image of the full volume has a high frame rate (20 fps, for example) equal to that of the sub volumes, and thus it is possible to produce a three-dimensional moving image in real time for even a moving region such as a heart under examination for diagnosis.

Figure 2:
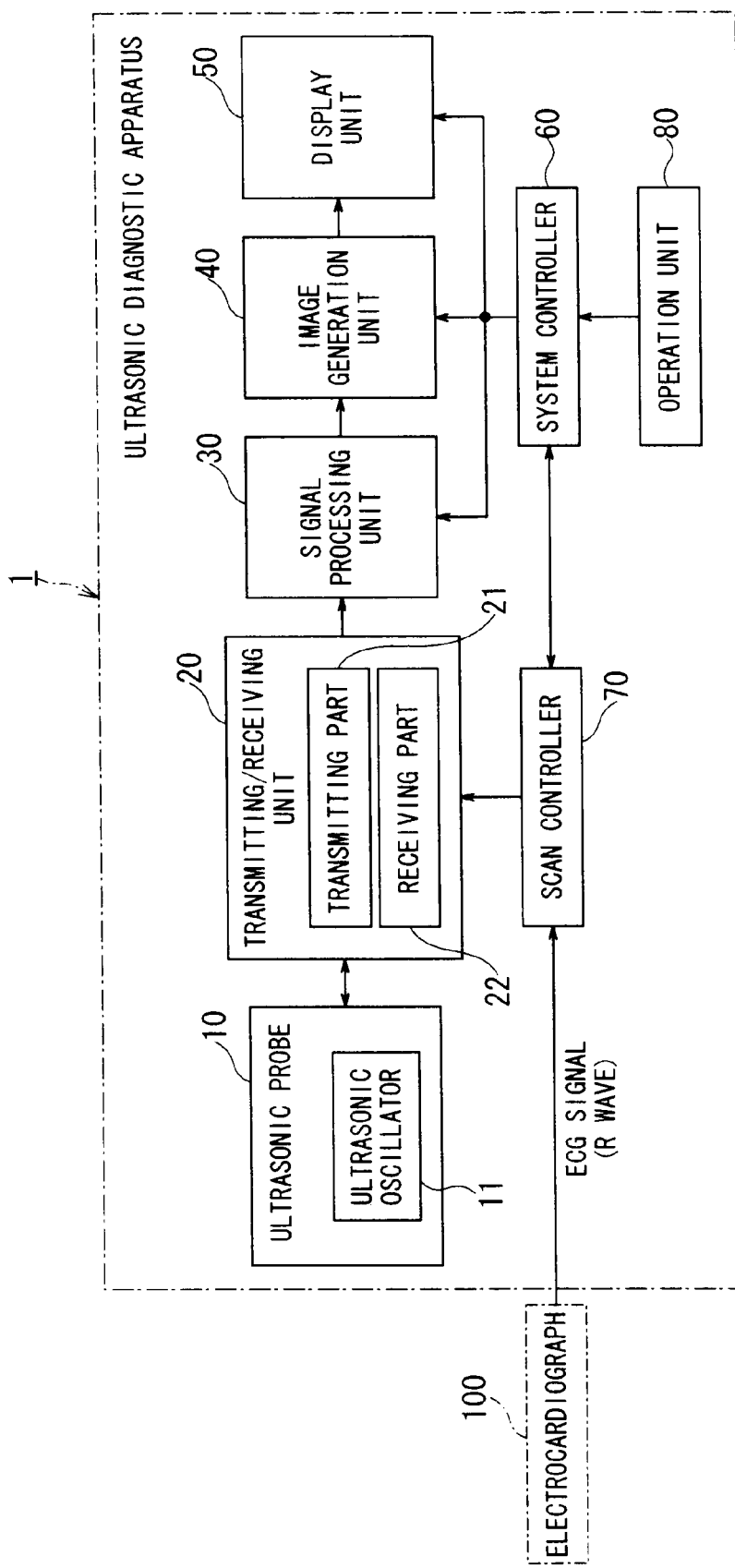
FIG. 2 is a block diagram illustrating an example of a configuration of an ultrasonic diagnostic apparatus according to an embodiment of the present invention.

FIG. 2 is a block diagram illustrating an example of a configuration of the ultrasonic diagnostic apparatus 1. The ultrasonic diagnostic apparatus 1 includes an ultrasonic probe 10, a transmitting/receiving unit 20, a signal processing unit 30, an image generation unit 40, a display unit 50, a system controller 60, a scan controller 70, and an operation unit 80.

The ultrasonic probe 10 has a plurality of ultrasonic oscillators 11 arranged in the form of an array thereby to generate an ultrasonic pulse in accordance with a transmission pulse signal output from a transmitting part 21 of the transmitting/receiving unit 20 so that the generated ultrasonic pulse is transmitted toward a body under examination. If the ultrasonic probe 10 receives an ultrasonic reflection signal reflected from the body under examination, the ultrasonic probe 10 converts it into an electric signal and supplies the resultant electric signal to a receiving part 22 of the transmitting/receiving unit 20. In accordance with a beam scanning control signal output from the scan controller 70, the ultrasonic probe 10 scans the ultrasonic beam in the main scanning direction and the sub scanning direction.

The transmitting part 21 of the transmitting/receiving unit 20 generates the transmission pulse to be supplied to each ultrasonic oscillator 11 in accordance with a timing signal or the like generated by the scan controller 70. Furthermore, in accordance with the beam scanning control signal generated by the scan controller 70, the transmitting part 21 of the transmitting/receiving unit 20 sets a delay for each transmission pulse so as to define the scanning direction of the transmission ultrasonic beam.

If the reflection signal from the body under examination is supplied from each ultrasonic oscillator 11 to the receiving part 22 of the transmitting/receiving unit 20, the receiving part 22 of the transmitting/receiving unit 20 amplifies the received reflection signal and converts it from analog form into digital form. Furthermore, based on the beam scanning control signal generated by the scan controller 70, the receiving part 22 of the transmitting/receiving unit 20 sets a delay for the reflection signal of each ultrasonic oscillator 11 so as to determine the scanning direction of the received ultrasonic beam, and the receiving part 22 of the transmitting/receiving unit 20 adds the delay to each reflection signal. The resultant signal is supplied as a reflection signal of the beam to the signal processing unit 30.

The signal processing unit 30 performs signal processing such as a filtering process on the reflection signal supplied from the receiving part 22 and outputs the resultant signal to the image generation unit 40.

The image generation unit 40 generates three-dimensional image data from the reflection signal corresponding to the beam scanning position. Note that in the present embodiment, the ultrasonic diagnostic apparatus 1 generates image data for each of the sub volumes and produces synthesized three-dimensional image data of the full volume from images of the respective sub volumes. The process of producing the synthesized three-dimensional image data is performed in conjunction with the operation of the scan controller 70 as will be described in detail later.

The image generation unit 40 performs processing such as a rendering process on the synthesized three-dimensional image data of the full volume thereby to generate a three-dimensional image viewed in a specified arbitrary direction or an image of a specified arbitrary section thereof. The generated image data is output to the display unit 70. The three-dimensional image data may be provided in the form of a moving image that is updated every frame time, for example, at 20 fps. The moving image data can be output in real time to the display unit 70 during diagnosis. The image data may be stored in a memory, and the moving image may be output in an off-line mode after diagnosis, or a still image extracted from the moving image may be output.

The display unit 70 is a display device such as a liquid crystal display configured to display the image output from the image generation unit 40 and various kinds of parameters for use in diagnosis.

The operation unit 80 is a man-machine interface that allows a user to set various diagnosis modes of the ultrasonic diagnostic apparatus 1 and various parameters associated with the respective diagnosis modes. In the present embodiment, the ultrasonic diagnostic apparatus 1 has a diagnosis mode in which motion of a beating heart can be displayed in the form of a three-dimensional moving image in synchronization with the ECG trigger signal (hereinafter, referred to as a triggered three-dimensional diagnosis mode). The ultrasonic diagnostic apparatus 1 is also operable in a conventional two-dimensional diagnosis mode. The setting as to the respective diagnosis modes and switching between them are performed via the operation unit 80.

The system controller 60 controls the whole ultrasonic diagnostic apparatus 1 in accordance with the diagnosis mode and various parameters set via the operation unit 80.

The scan controller 70 performs beam management on the ultrasonic beam and transmission/reception time management depending on the diagnosis mode. More specifically, in the triggered three-dimensional diagnosis mode, the scan controller 70 generates an ECG trigger signal (trigger signal) from an ECG signal (R wave) output from an electrocardiograph 100 and determines the beam scanning position (the main scanning direction and the sub scanning direction) for each sub volume in synchronization with the trigger signal and also determines various parameters associated with the repetitive scanning operation in the sub volume. The signals and the parameters are supplied to the transmitting/receiving unit 20 or the image generation unit 40. Furthermore, the scan controller 70 determines the various parameters associated with the transmission pulse such as the pulse repetition frequency of the ultrasonic beam and generates various timing signals based on the parameters of the transmission pulse.

(2) Operation in Triggered Three-Dimensional Diagnosis Mode

The operation of the ultrasonic diagnostic apparatus 1 configured in the above-described manner is described below, in particular, on the operation in the triggered three-dimensional diagnosis mode.

Figure 3:
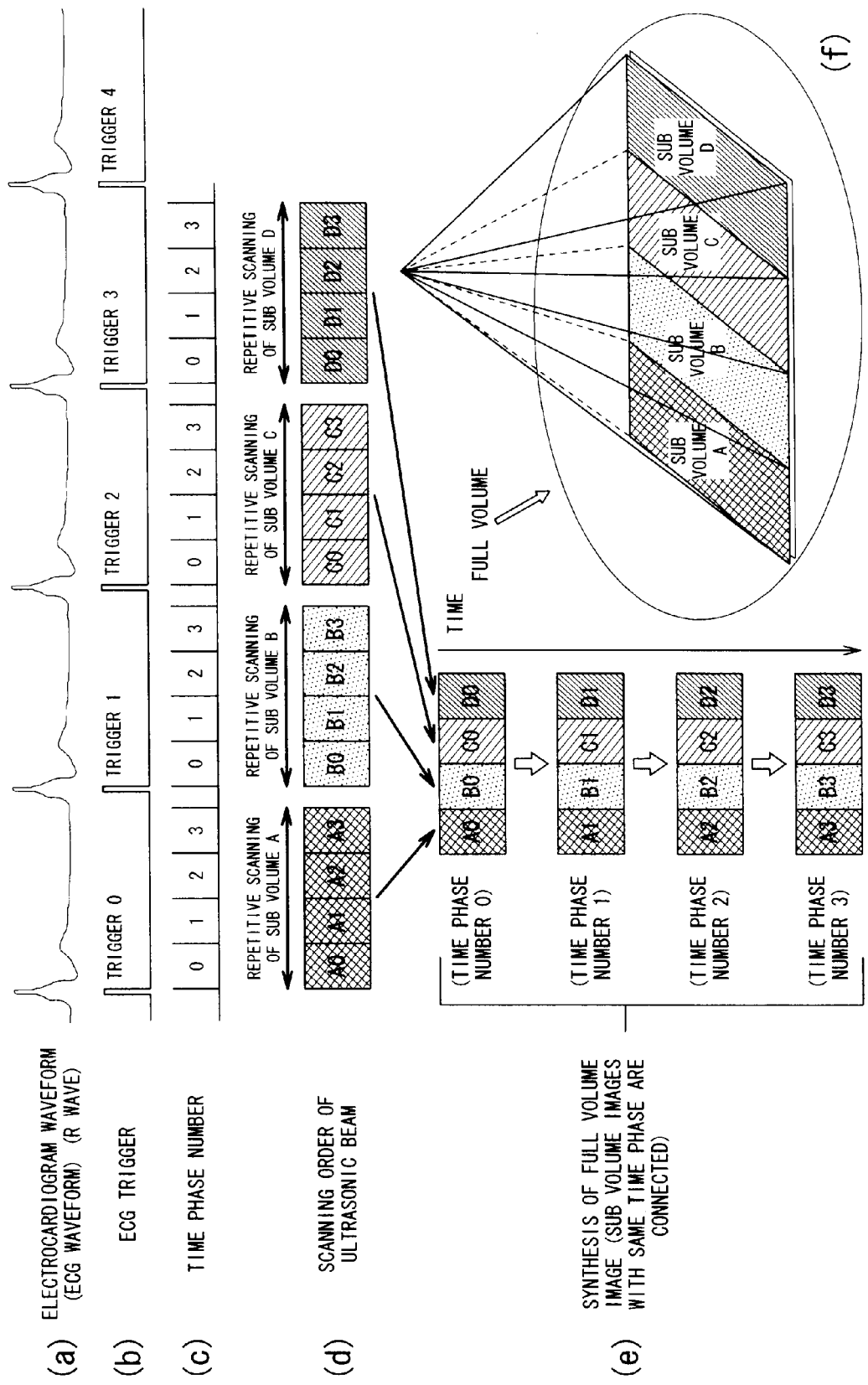
FIG. 3 is a diagram illustrating a concept of a general operation in a triggered three-dimensional diagnosis mode (for a full volume scanning with dividing into sub volumes)

FIG. 3 illustrates the principle of the operation in the triggered three-dimensional diagnosis mode disclosed, for example, in U.S. Pat. No. 6,544,175. The triggered three-dimensional diagnosis mode is used mainly in diagnosis of a heart. In the triggered three-dimensional diagnosis mode, motion of a beating heart can be displayed as a three-dimensional moving image. In the triggered three-dimensional diagnosis mode, an ECG signal varying depending on the beat of a heart of a patient is input from the electrocardiograph 100, and a pulse signal called the ECG trigger signal is generated from the input ECG signal. As for the ECG signal, an R wave signal (see (a) in FIG. 3) having a form of a pulse that is output in an end period of diastole is generally used. The ECG signal is input to the scan controller 70. The scan controller 70 generates the ECC trigger signal by applying a properly determined threshold value to the input ECG signal (see (b) in FIG. 3). The ECG trigger signal is a signal synchronous with beating of a heart. When the heart beats 60 times every minute, the ECG trigger signal has a repetition period of 1 second.

In the triggered three-dimensional diagnosis mode, the whole diagnosis region (full volume) is divided into a plurality of sub volumes (blocks) and the sub volumes are sequentially scanned in response to one ECG trigger signal. For example, as shown in (f) of FIG. 3, the full volume is divided into four sub volumes A, B, C, and D, and the sub volumes are scanned sequentially in the order A, B, C, D in response to ECG trigger signals 0, 1, 2, and 3.

Each sub volume is scanned not once but a plurality of times (N times). In the example shown in FIG. 3, the scanning is performed 4 times (N=4). The scanning time T needed to scan each sub volume once corresponds to the frame time (the reciprocal of the frame rate) of a moving image as described in further detail later, and thus, to obtain a smooth moving image, it is desirable that the scanning time T be about 50 ms (=1/20 fps) or smaller. If it is assumed that the repetition period of the ECG trigger signal is 1 second and the unit scanning time is 50 ms, then the number of repetitions of scanning for each sub volume becomes 20 (N=20). In the example shown in FIG. 3, for the purpose of simplicity of explanation, the number of repetitions of scanning for each sub volume is assumed to be 4 (N=4).

When the same sub volume is being scanned repeatedly, the heart periodically beats, and thus image data generated during the repetitive scanning process is different depending on the time phase, i.e., the delay with respect to the ECG trigger.

In (c) of FIG. 3, time phases are defined for the respective scan repetition periods and time phase numbers are assigned to the respective time phases in the order "0", "1", "2", "3" starting from the time phase closest to the ECG trigger signal. In (c) of FIG. 3, each of the scanning periods of the sub volumes are identified by a combination of a phase number (one of "0", "1", "2", and "3") and a sub volume name (one of "A", "B", "C", and "D") such as "A0" to "A3", "B0" to "B3", "C0" to "C3", and "D0" to "D3", and the scanning periods are arranged in the order in which they are scanned with the ultrasonic beam.

The signal processing unit 30 performs signal processing on the reflection signal received from the body under examination and outputs, in real time, the resultant reflection signal to the image generation unit 40 in the order corresponding to the scanning order.

In (e) of FIG. 3, a manner of synthesizing a full volume in a process performed by the image generation unit 40 is shown. The image generation unit 40 extracts data with an equal time phase number from the data of the sub volumes identified by the time phase numbers, and connects the data corresponding to the sub volumes A, B, C, and D so as to obtain synthesized data of the full volume. Note that even for sub volume data having an equal time phase number, there is a time difference corresponding to one period of the ECG trigger signal between adjacent sub volumes. However, the change in shape of the heart can be regarded as having the same periodicity as that of the ECG trigger signal, and thus the full volume image obtained by connecting the sub volumes with the same time phase number has good spatial continuity.

At a time when data of the sub volume "D0" corresponding to the time phase number "0" is acquired, data of the sub volumes "A0", "B0", and "C0" has already been acquired. Thus, at this point of time, the full volume image corresponding to the time phase number "0" is generated.

At a time when next data of the sub volume "D1" corresponding to the time phase number "1" is acquired, data of the sub volumes "A1", "B1", and "C1" has already been acquired. Thus, at this point of time, the full volume image corresponding to the time phase number "1" is generated. Subsequently, full volume images for time phase numbers 2 and 3 are generated in a similar manner.

If the scanning "D3" for the sub volume D is completed, the scanning is repeated from the sub volume A. In this case, the data "A0" obtained in this scanning operation replaces the full volume data "A0" with the time phase number "0" generated in the previous scanning, and thus the full volume image with the time phase number "0" is updated.

As described above, the full volume image is generated and updated every one scanning period of each sub volume (hereinafter referred to as a scan repetition period $T_{SV}$).

The technique described above allows the obtained image to be seemed as if the whole full volume were scanned every one scanning period of one sub volume although the actual scanning time for the whole full volume is longer. That is, it is possible to obtain a full volume image updated at a frame rate that is apparently, but not actually, equal to the frame rate of sub volumes.

For example, when the highest possible frame rate of the full volume is limited to 5 fps due to a limitation on the scanning time, if the full volume is divided into four sub volumes, it is allowed to scan each sub volume in a scanning period that is one-fourth the scanning time for the full volume, and thus the frame rate of sub volume image becomes 20 fps that is 4 times greater than that of the full volume image. In the triggered three-dimensional diagnosis mode, the frame rate of the full volume image is equal to the frame rate of the sub volume image, and thus it is possible to achieve the frame rate as high as 4 times the frame rate achieved in the conventional technique.

As described above, in the triggered three-dimensional diagnosis mode, it is possible to obtain a high-resolution image with a high frame rate for a great three-dimensional diagnostic region, and thus it is possible to generate a real-time moving image for a moving diagnostic object such as a heart.

However, in the conventional triggered three-dimensional diagnosis mode, as described above, the scan repetition period is set to a predetermined fixed value. Therefore, if the interval of the ECG trigger signal, i.e., the heartbeat period $T_{ECG}$ is not equal to an integral multiple of the predetermined constant scan repetition period, the scanning operation in a repetition period immediately before the arrival of an ECG trigger signal is aborted in the middle of that period.

Figure 4:
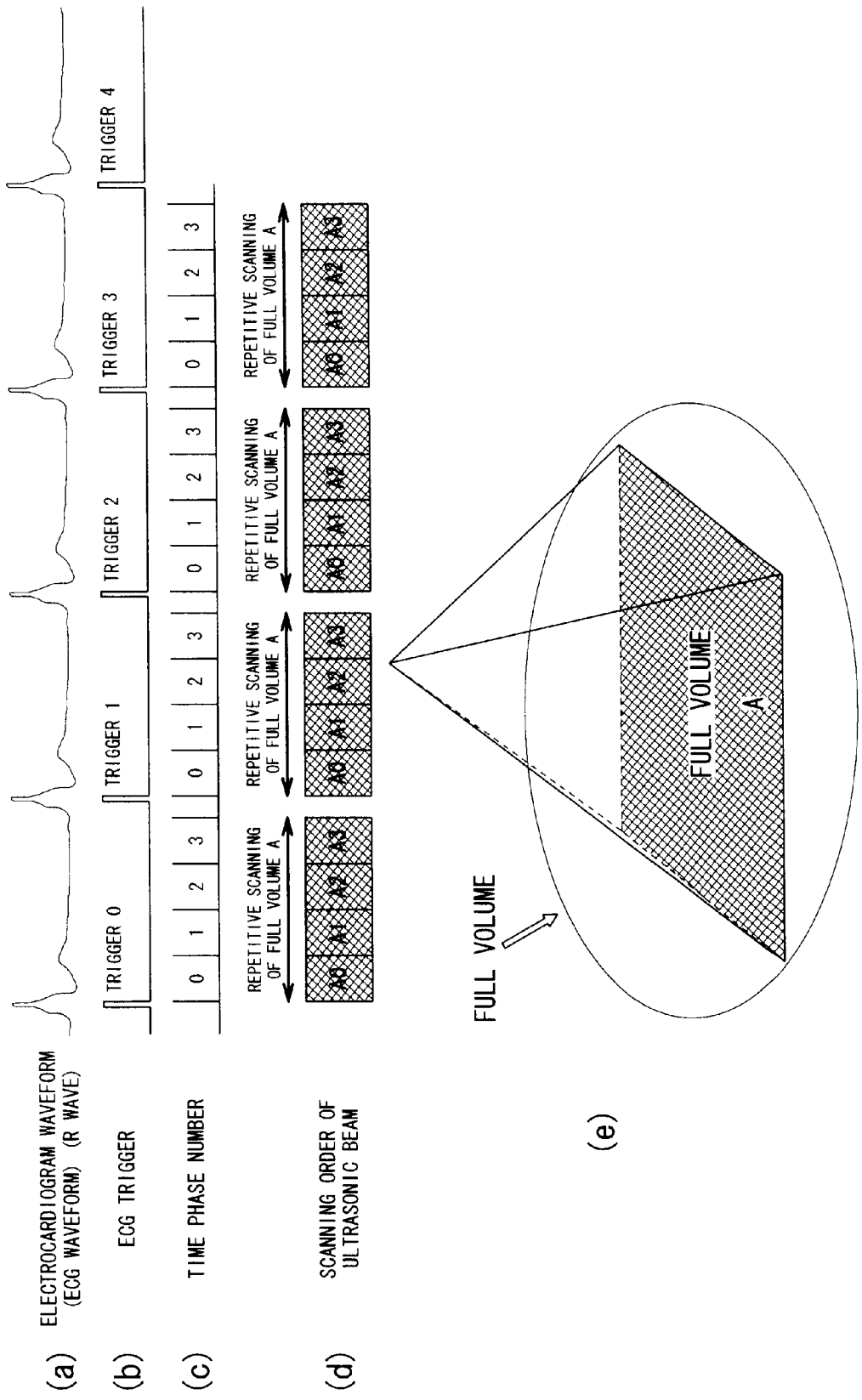
FIG. 4 is a diagram illustrating a concept of a general operation in a triggered three-dimensional diagnosis mode (for a full volume scanning without dividing into sub volumes)

If the scanning time for the full volume can be decreased by, for example, increasing the number of beams which are capable of receiving signals simultaneously from different positions, a sufficiently high frame rate can be obtained without dividing the full volume into a plurality of the sub volume. In FIG. 4, a full volume A is scanned without dividing into sub volumes, while using the ECG trigger signal, is illustrated. Even in this case, the same problem also arises. That is, when the heartbeat period $T_{ECG}$ is not equal to an integral multiple of the predetermined constant scan repetition period, the scanning operation in a repetition period immediately before the arrival of an ECG trigger signal is aborted in the middle of that period.

Figure 5:
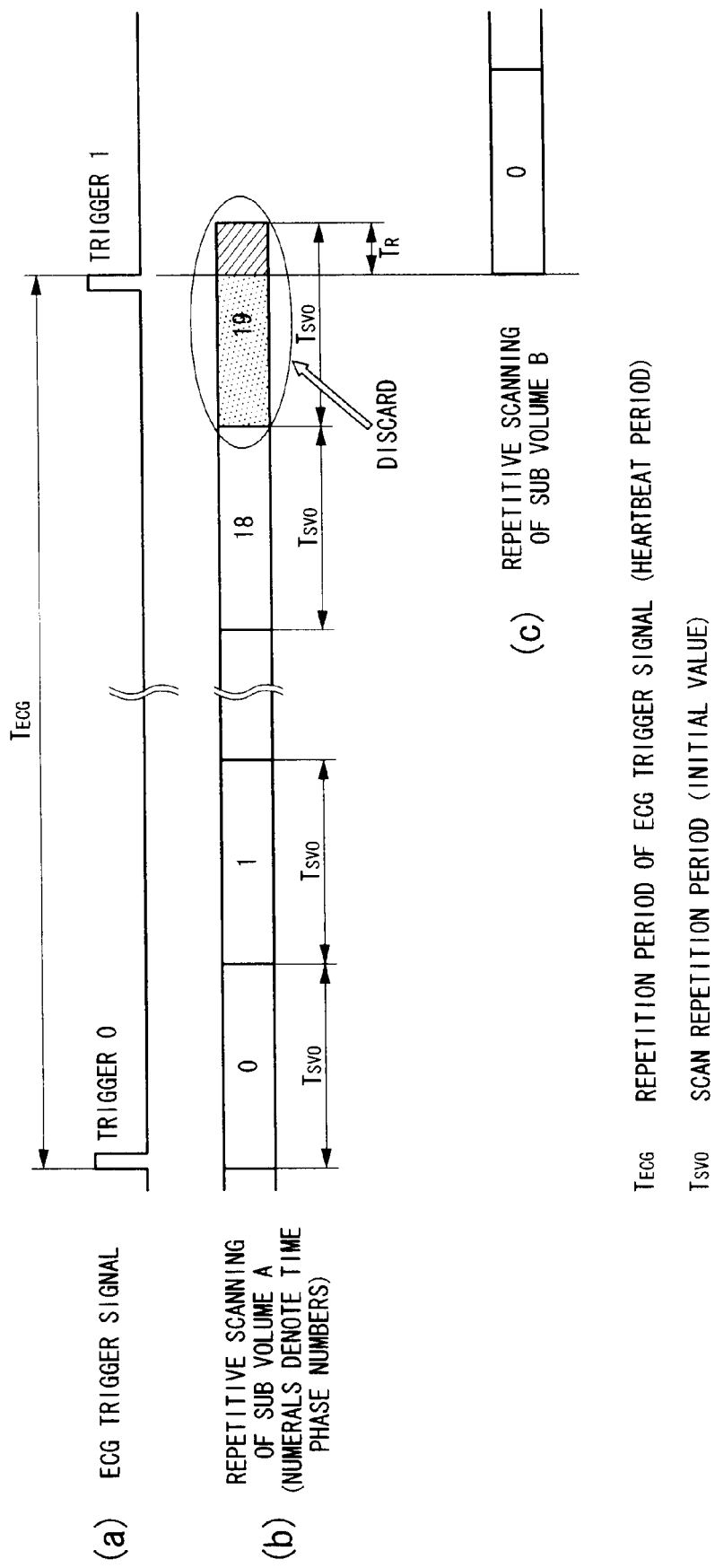
FIG. 5 is a diagram illustrating a problem in a conventional triggered three-dimensional diagnosis mode.

With reference to FIG. 5, the problem described above is described in further detail below. In the following descriptions, the case where the sub volume is scanned is taken as an example; however, the case where the full volume is scanned without dividing into the sub volumes is not excluded.

In FIG. 5, (a) illustrates an ECG trigger signal with a repetition period equal to a heartbeat period $T_{ECG}$. In FIG. 5, (b) illustrates a manner in which the sub volume A is scanned repeatedly. In this example, the sub volume A is to be scanned with a constant period $T_{SVO}$ (hereinafter, referred to as an initial scan repetition period $T_{SVO}$) 20 times (from time phase number 0 to time phase number 19).

However, the heartbeat period $T_{ECG}$ is not necessarily equal to an integral multiple of the initial scan repetition period $T_{SVO}$. Therefore, a next ECG trigger signal (trigger 1) comes a remaining time $T_R$ before the end of the last scan repetition period (time phase number 19). In response to the arrival of the ECG trigger signal (trigger 1) the scanning of the sub volume A is stopped and scanning of the sub volume B is started (see (c) in FIG. 5). As a result, the data of the period with the time phase number 19 is incomplete, and it cannot be used in synthesis of the full volume image.

In the ultrasonic diagnostic apparatus 1 according to the present embodiment, to avoid the above problem, the scan repetition period is not fixed, but a variable scan repetition period $T_{SV}$ is employed. More specifically, the scan repetition period $T_{SV}$ is determined so that an integral multiple of the scan repetition period $T_{SV}$ is equal to the heartbeat period $T_{ECG}$, and the operation in the triggered three-dimensional diagnosis mode is performed using the scan repetition period $T_{SV}$ instead of the initial scan repetition period $T_{SVO}$.

Figure 6:
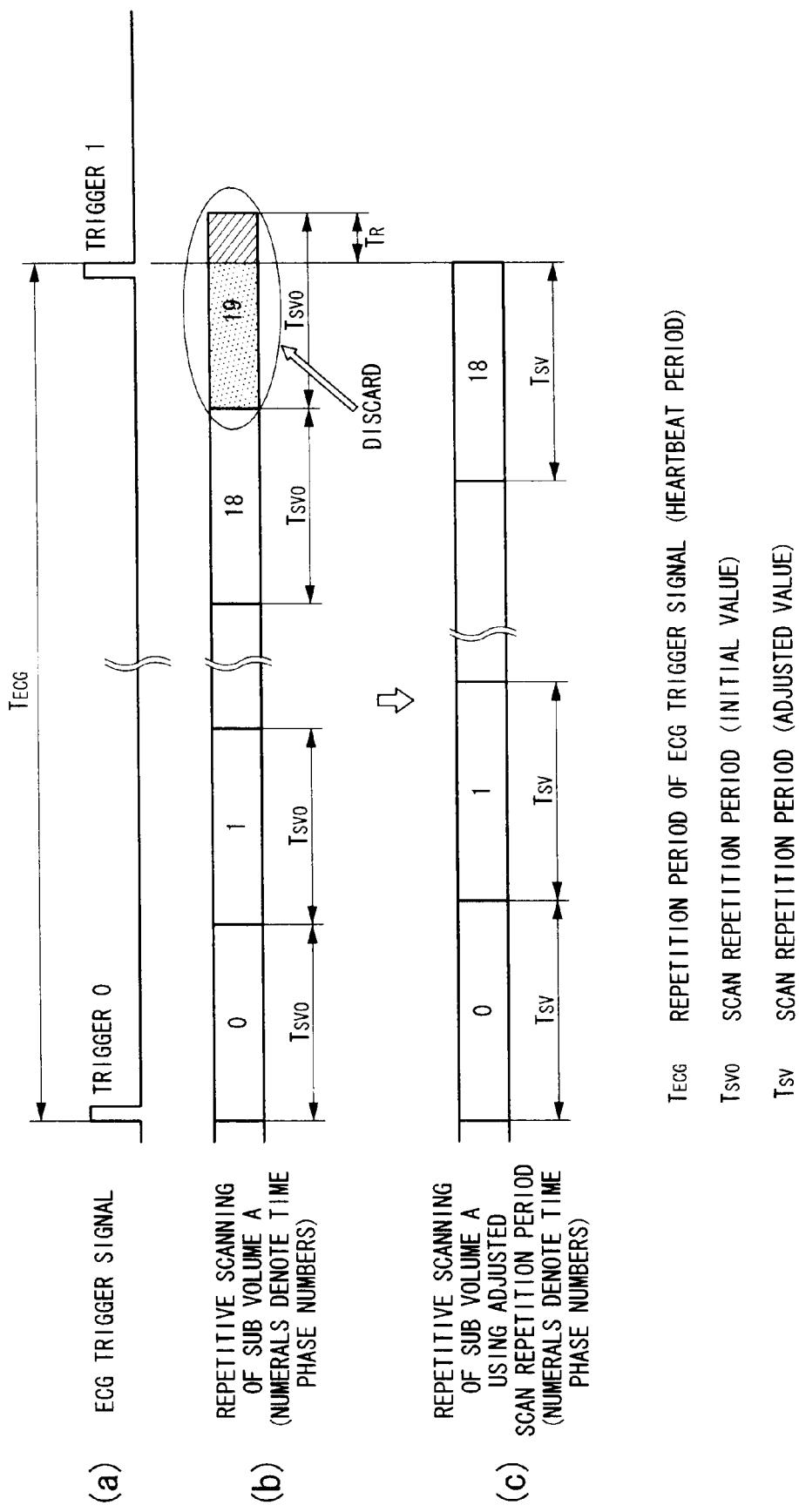
FIG. 6 is a diagram illustrating a concept of an operation of an ultrasonic diagnostic apparatus in a triggered three-dimensional diagnosis mode according to an embodiment of the present invention.

The basic concept of this technique is described in further detail below with reference to FIG. 6. In FIG. 6, (b) illustrates a scanning operation using the unadjusted initial scan repetition period $T_{SVO}$, while (c) illustrates a scanning operation using an adjusted scan repetition period $T_{SV}$.

In the scanning operation using the adjusted scan repetition period $T_{SV}$, because the scan repetition period $T_{SV}$ is adjusted so as to be equal to an integral multiple of the heartbeat period $T_{ECG}$, scanning is performed completely for all scanning periods from the time phase number 0 to the time phase number 18 without having an incomplete scanning period. Thus, it is possible to acquire complete data associated with motion of the heart even in the period immediately before the trigger 1. A method of adjusting the scan repetition period is described in further detail below.

(3) Adjusting of Scan Repetition Period (According to First Method)

Figure 7:
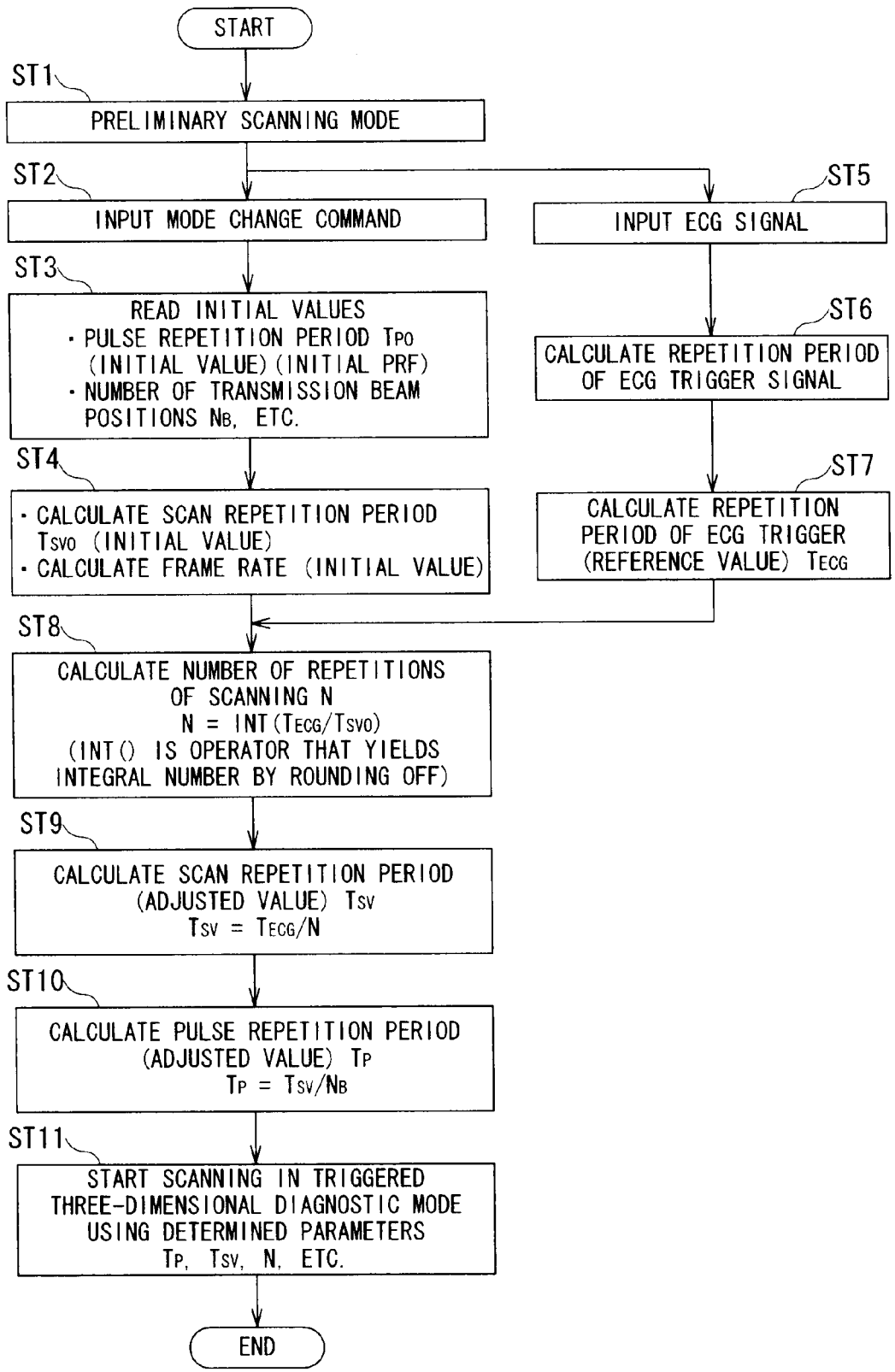
FIG. 7 is a flow chart illustrating an example of a method (first method) of adjusting a scan repetition period.
Figure 9:
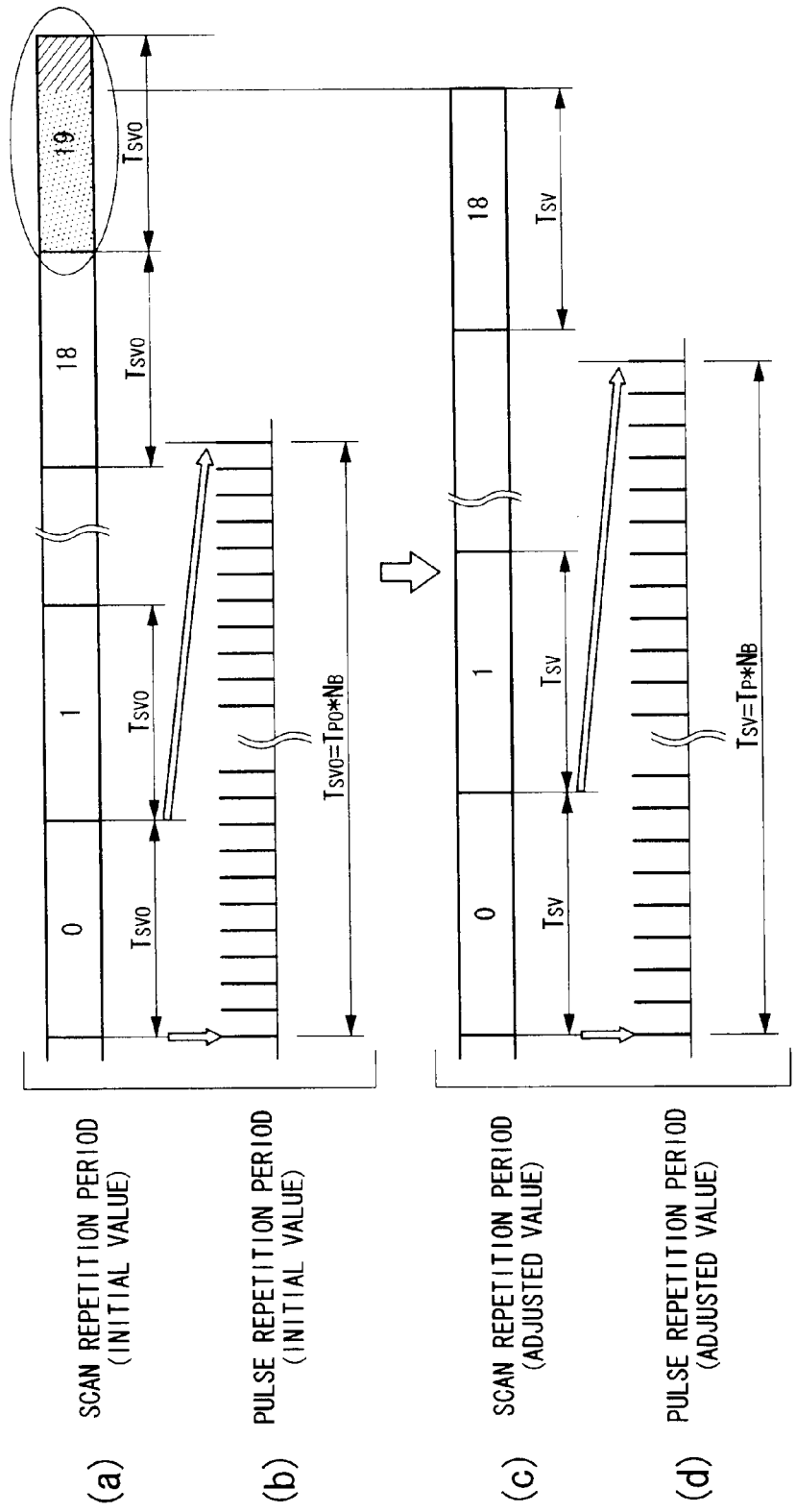
FIG. 9 is a diagram illustrating a process of adjusting a scan repetition period according to a first method.

FIG. 7 is a flow chart illustrating an example of a process of adjusting the scan repetition period according to a first method, and FIG. 9 illustrates a manner in which this process is performed. Note that the process is performed mainly by the scan controller 70. In this first method, the scan repetition period $T_{SV}$ is adjusted by equally changing the pulse repetition period $T_P$ of transmission pulses in the scan repetition period $T_{SV}$. Note that the pulse repetition period $T_P$ is the reciprocal of the pulse repetition frequency.

In the ultrasonic diagnostic apparatus 1 according to the present embodiment, before the operation enters the triggered three-dimensional diagnosis mode, two-dimensional scanning is performed in a preliminary scanning mode (step ST1).

Figure 8A:
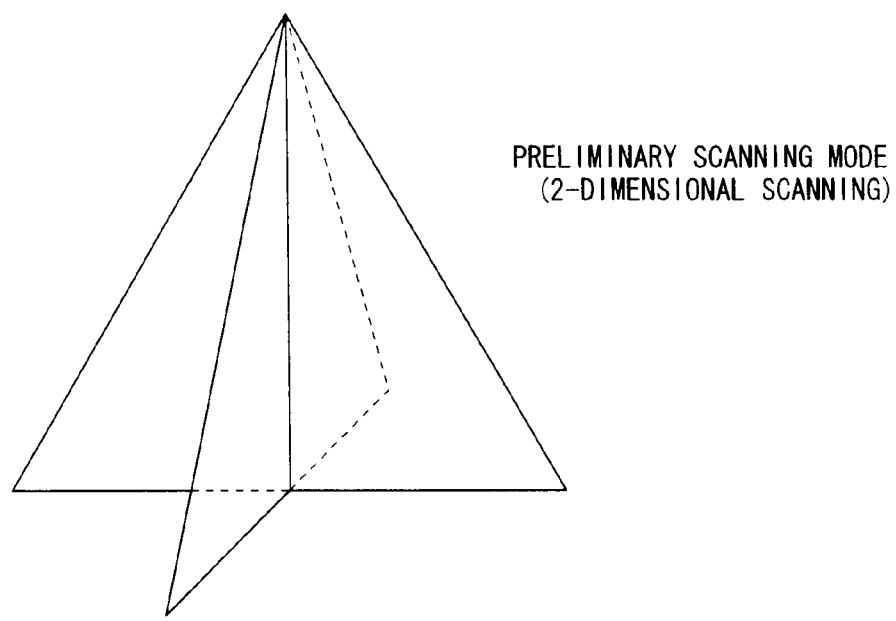
FIG. 8A is a diagram illustrating a concept of scanning in a preliminary scanning mode.
Figure 8B:
FIG. 8B is a diagram illustrating a concept of switching into a triggered three-dimensional diagnosis mode.
Figure 8B:
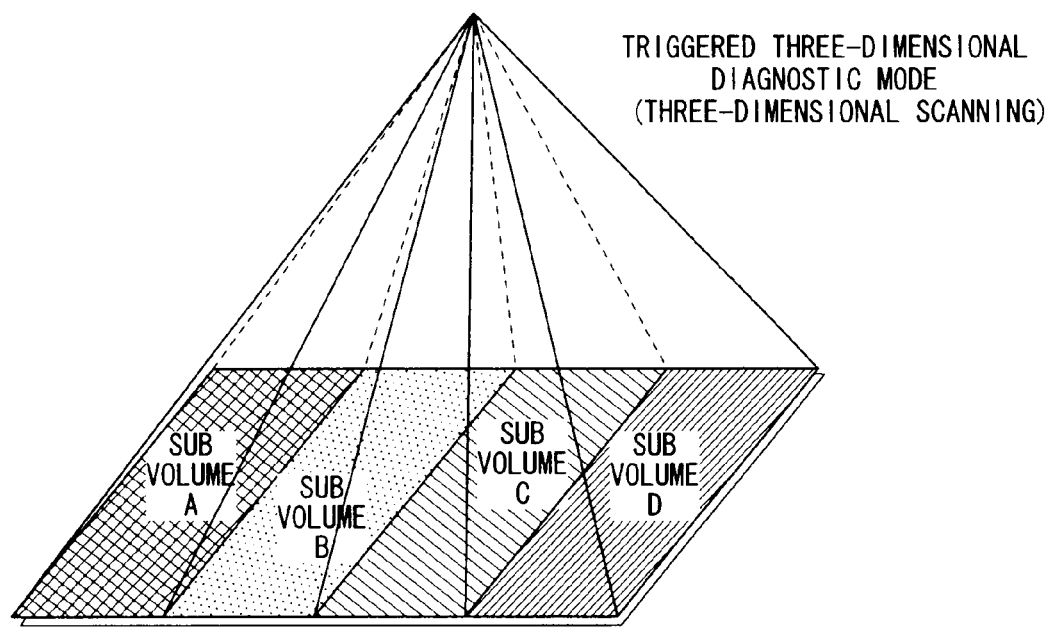

FIG. 8A illustrates an example of a manner in which two-dimensional scanning is performed in the preliminary scanning mode. In the preliminary scanning mode, the ultrasonic beam is scanned alternately in two planes perpendicular to each other, and two images obtained from the respective scanning planes are displayed on the display unit 50. The main purpose of the preliminary scanning mode is positioning of the ultrasonic probe 10. That is, based on the two images obtained in the preliminary scanning mode, it is checked whether the ultrasonic probe 10 is in a proper position with respect to a part of a body to be examined in the triggered three-dimensional diagnosis mode. In the preliminary scanning mode, the scanning is performed only for the two planes, and thus the scanning time for the whole range is very short compared with the scanning time (three-dimensional scanning time) in the triggered three-dimensional diagnosis mode. Therefore, a high frame rate is possible in the preliminary scanning mode. The high frame rate makes it possible to easily find a part to be examined while moving the ultrasonic probe 10.

In the preliminary scanning mode, an ECG trigger signal is also input (step ST5 in FIG. 7) and the repetition period of the ECG trigger signal (the heartbeat period $T_{ECG}'$) is detected (step ST6). The detected heartbeat period $T_{ECG}'$ is multiplied by a factor K (K≦1), and the reference value of the ECG trigger period $T_{ECG}$ (i.e., the reference value based on the period of the trigger signal), based on which to change parameters including the scan repetition period $T_{SV}$, is determined (step ST7). The factor K is a margin factor to handle a change in the heartbeat period and is preferably set to about 0.9. In the following description, for the purpose of simplicity of explanation, it is assumed that K=1. That is, the term "heartbeat period $T_{ECG}$" is used without distinguishing between the heartbeat period $T_{ECG}'$ and the reference value of the ECG trigger period $T_{ECG}$.

During the operation in the preliminary scanning mode, if a command to switch the operation into the triggered three-dimensional diagnostic mode is input via the operation unit 80 (step ST2), initial values are read from a memory (step ST3). The initial values read in step ST3 include, for example, an initial pulse repetition period $T_{PO}$ (or initial PRFo), the number of transmission positions $N_B$, etc.

The initial pulse repetition period $T_{PO}$ is a value predetermined depending on the depth of the part to be examined for diagnosis. For example, the initial pulse repetition period $T_{PO}$ is set such that $T_{PO}$=200 μs ($P_{RFO}$=5000 Hz).

The number of transmission beam positions $N_B$ is a value predetermined depending on the area size of the part to be examined for diagnosis. For example, the number of transmission beam positions $N_B$ is set such that $N_B$=261 (29 lines in the main scanning direction (AZ direction) and 9 lines in the sub scanning direction (EL direction)).

Next, the initial scan repetition period $T_{SVO}$ and the scan repetition rate, which is the reciprocal of the initial scan repetition period, are calculated (step ST4). The scan repetition rate is substantially equal to the frame rate of the moving image. Hereinafter, the reciprocal of the scan repetition period $T_{SV}$ is referred to as the frame rate $FR_{SV}$, and the initial value thereof is referred to as the initial frame rate $FR_{SVO}$.

The initial scan repetition period $T_{SVO}$ can be determined according to the following equation (see (b) in FIG. 9):

$$T_{SVO}=T_{PO}*N_B$$

Substituting the values described above into this equation yields the initial scan repetition period $T_{SVO}$ as $T_{SVO}=T_{PO}*N_B$=200 μs*261=52.2 ms. Furthermore, the initial frame rate $FR_{SVO}$ is calculated as $FR_{SVO}$=1/$T_{SVO}$=1/52.2 ms=19.2 fps.

Next, a calculation is performed to determine the number of repetitions of scanning N that allows data to be completely acquired without yielding incomplete data for the heartbeat period $T_{ECG}$ calculated from the heart rate detected in the preliminary scanning mode (step ST8). More specifically, the number of repetitions of scanning N is calculated, for example, as N=int($T_{ECG}$/$T_{SVO}$), where int( ) is an operator that yields an integer by rounding off a given value.

In the examples shown in (b) and (c) in FIG. 6 and (a) and (c) in FIG. 9, the number of repetitions of scanning N is determined as 19 (corresponding to time phase numbers 0 to 18) by performing the above-described calculation.

In next step ST9, the scan repetition period $T_{SV}$ is determined such that $T_{SV}$ is equally distributed over the whole heartbeat period $T_{ECG}$ without yielding an incomplete period or a remaining period. The scan repetition period $T_{SV}$ can be calculated, for example, according to an equation:

$$T_{SV}=T_{ECG}/N.$$

The adjusted scan repetition period $T_{SV}$ used in (c) of FIG. 6 or (c) of FIG. 9 is determined by performing the calculation described above.

In step ST10, the scan repetition period $T_{SV}$ is divided by the number of transmission beam positions $N_B$ thereby determining the transmission pulse repetition period $T_P$ equally distributed over the scan repetition period $T_{SV}$. The transmission pulse repetition period $T_P$ can be determined according to an equation (see (d) of FIG. 9):

$$T_P=T_{SV}/N_B.$$

Finally, the scanning in the triggered three-dimensional diagnosis mode is started using the parameters determined in steps ST8 to ST19, i.e., the number of repetitions of scanning N, the scan repetition period $T_{SV}$, the transmission pulse repetition period $T_P$, etc. (step ST11).

In a case where the heart rate is measured as 74 bpm (beats per minute) in the preliminary scanning mode, the heartbeat period $T_{ECG}$ is determined as about 810 ms by calculating the reciprocal of the heart rate (steps ST6 and ST7). On the other hand, as described above, the initial scan repetition period $T_{SVO}$ is given as $T_{SVO}=T_{PO}*N_B$=200 μms*261=52.2 ms.

If these values are applied to the integral number calculation process in step ST8, then the number of repetitions of scanning is calculated as N=int($T_{ECG}$/$T_{SVO}$)=int(810 ms/52.2 ms)=15.

In this case, the adjusted scan repetition period $T_{SV}$ is determined as about 53.8 ms. Thus, a remaining period of about 3 ms (810 ms−15*53.8 ms=3 ms) occurs in the heartbeat period 810 ms. On the other hand, the frame rate $FR_{SV}$ is determined as about 18.5 fps, and PRF is determined as 4844 Hz (the pulse repetition period $T_P$ is equal to about 206 μs).

On the other hand, in a case where the scan repetition period is not adjusted and the initial parameters are maintained, the initial scan repetition period $T_{SVO}$ is about 52.2 ms, and thus a remaining period of about 27 ms (810 ms−15*52.2 ms=27 ms) occurs in the heartbeat period 810 ms. In this case, the frame rate $FR_{SV}$ is about 19.2 fps, and PRF is 5000 Hz (the pulse repetition period $T_{PO}$ is 200 μs).

As described above, in the ultrasonic diagnostic apparatus 1 according to the present embodiment of the invention, by adjusting the scan repetition period $T_{SV}$, it is possible to greatly reduce the remaining period, in which useful data is not obtained, immediately before the ECG trigger signal, for example, from about 27 ms to about 3 ms.

In the process of determining the integral number in step ST8, the integral number may be determined by rounding up instead of rounding off. However, rounding up yields an adjusted scan repetition period shorter than the initial value, and thus the adjusted pulse repetition period also becomes shorter than its initial value. The reduction in the pulse repetition period causes a reduction in the depth of the part under examination for diagnosis compared with the targeted value (initial value).

In step ST8, in view of the above, the integral number is determined by rounding off, and the scan repetition period is adjusted to be longer than its initial value. Accordingly, the pulse repetition period is adjusted to be longer than its initial value. As a result, the adjusted pulse repetition period allows the depth of the part under examination to be greater than is allowed by the initial value, and thus it is ensured to acquire data at the targeted depth.

Figure 10A:
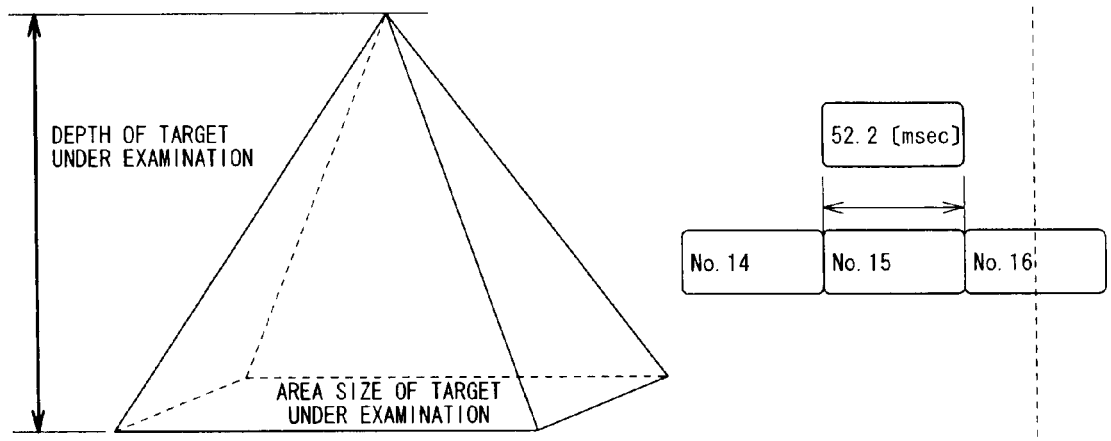
FIGS. 10A and 10B are diagrams illustrating a concept of adjusting a pulse repetition period in a scan repetition period according to a first method.
Figure 10B:
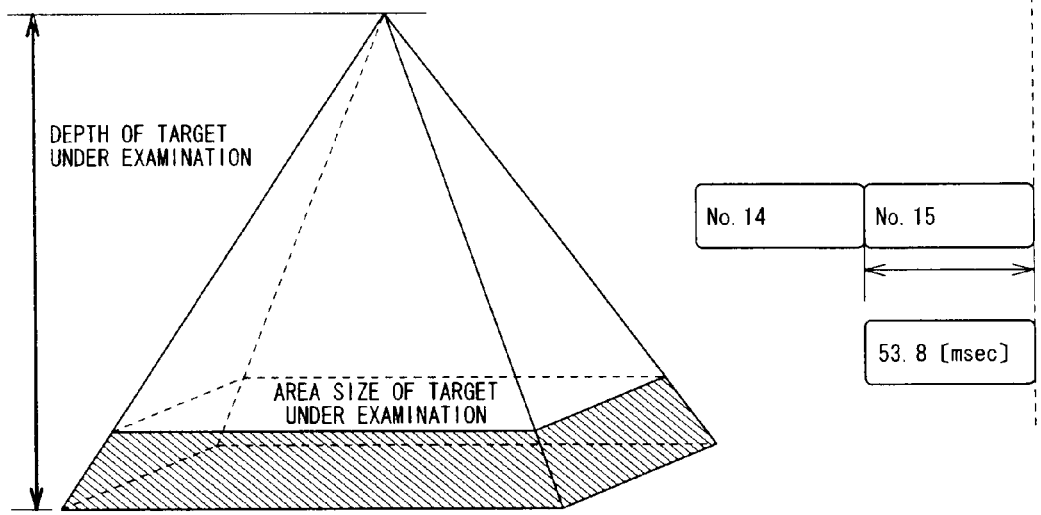

FIGS. 10A and 10B schematically illustrate a manner in which the above-described process is performed. FIG. 10A illustrates a state in which the parameters are not adjusted, and thus the scan repetition period $T_{SVO}$ is about 52.2 ms and the pulse repetition period $T_{PO}$ is about 200 μs. FIG. 10B illustrates a state in which the scan repetition period $T_{SV}$ is adjusted to about 53.8 ms and the pulse repetition period $T_P$ is adjusted about 206 μs. As a result of the increase in the pulse repetition period $T_P$ from the initial value of 200 μs to about 206 μs, the examinable depth is increased by an amount corresponding to a shaded region in FIG. 10B.

Figure 11A:
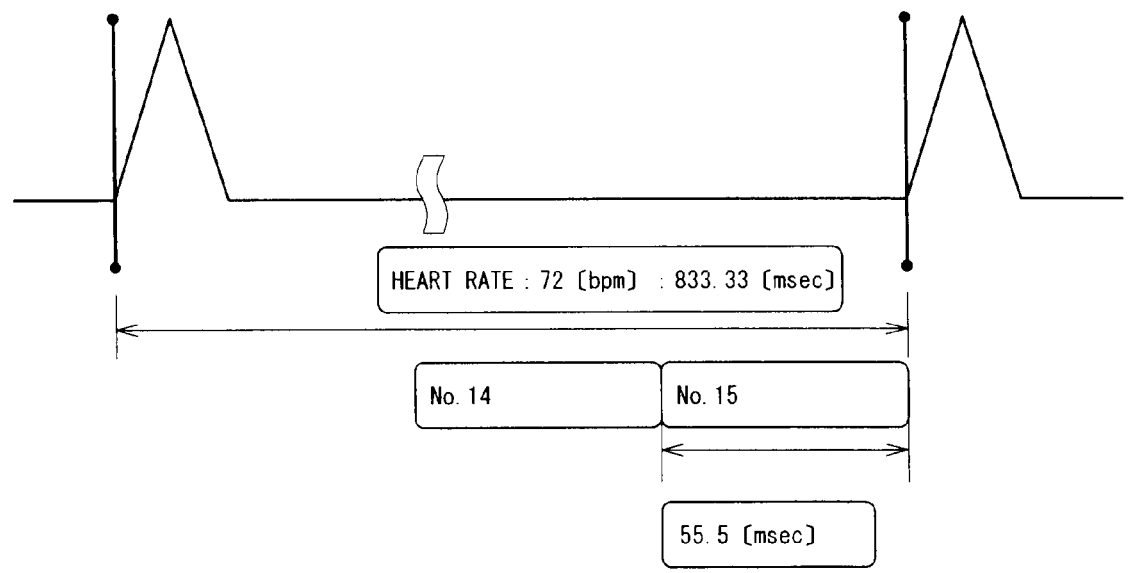
FIGS. 11A and 11B are diagrams illustrating a relationship between a heart rate and an adjusted scan repetition period for examples of parameter values.
Figure 11B:
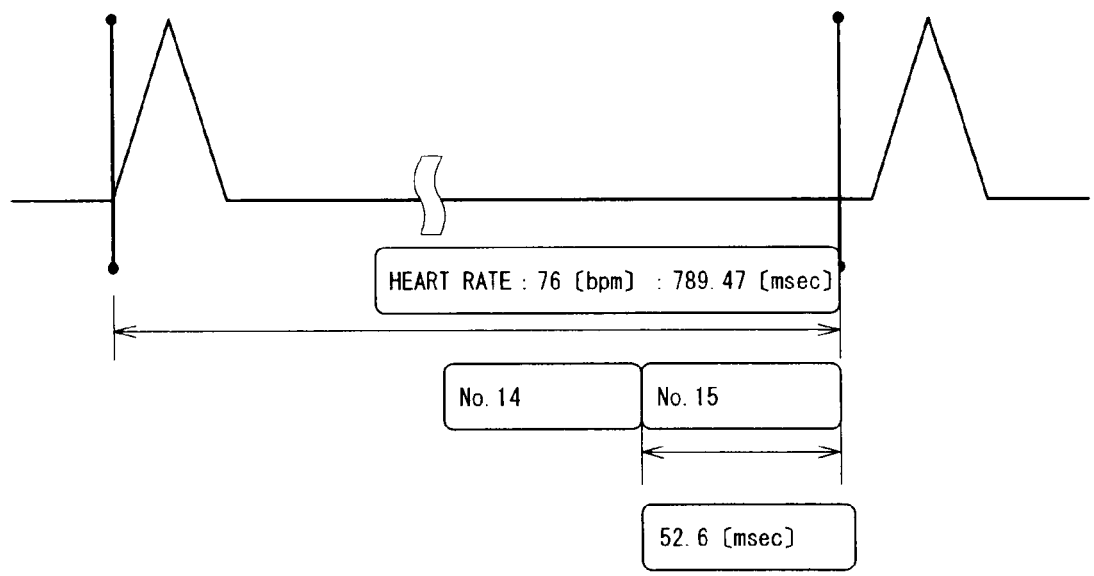

In the example shown in FIG. 10B, the heart rate is 74 bpm, and the scan repetition period $T_{SV}$ is adjusted to about 53.8 ms. FIGS. 11A and 11B illustrate examples of values of the scan repetition period $T_{SV}$ adjusted for different heart rates.

FIG. 11A illustrates an example in which the scan repetition period $T_{SV}$ is adjusted to about 55.5 ms for a heart rate of 72 bpm. In this case, the PRF is about 4699 Hz and the pulse repetition period $T_P$ is about 213 μs.

In the example shown in FIG. 11B, the scan repetition period $T_{SV}$ is adjusted to about 52.6 ms for a heart rate of 76 bpm. In this case, the PRF is about 4960 Hz and the pulse repetition period $T_P$ is about 202 μs.

For any heart rate, the pulse repetition period $T_P$ is longer than the initial value, i.e., 200 μs.

(4) Adjusting of Scan Repetition Period (According to Second Method)

Figure 12:
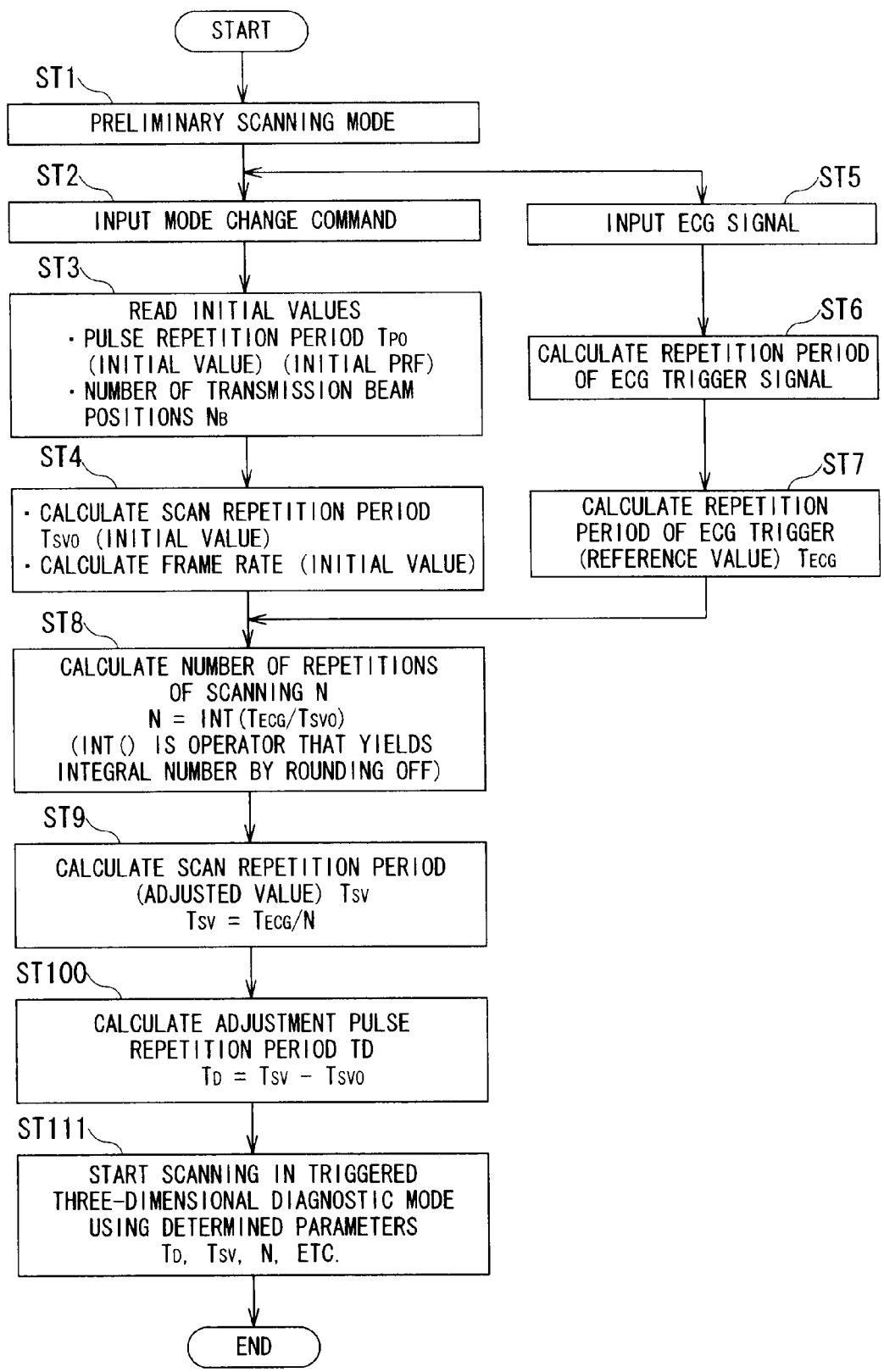
FIG. 12 is a flow chart illustrating an example of a method (second method) of adjusting a scan repetition period.
Figure 13:
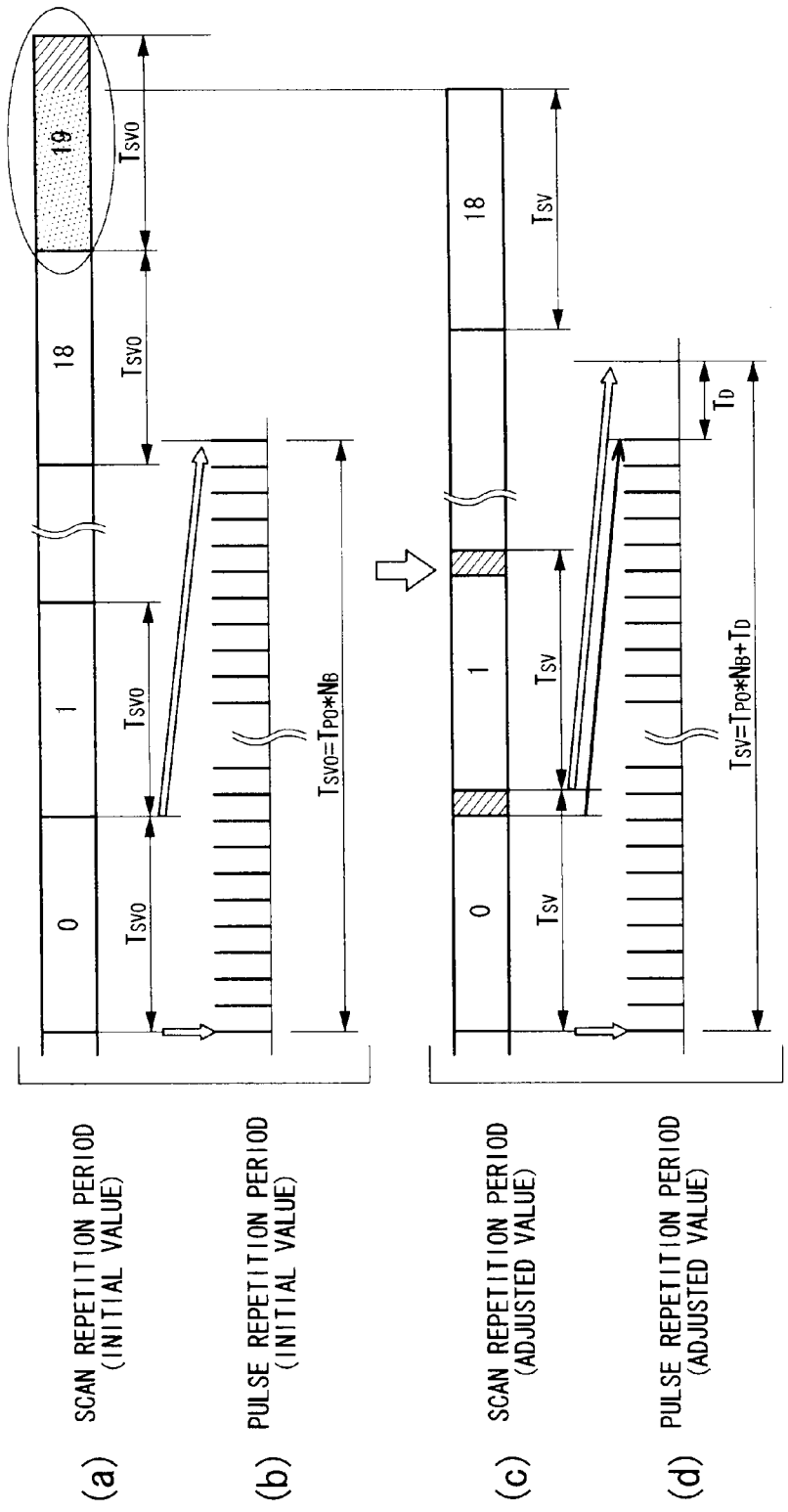
FIG. 13 is a diagram illustrating a process of adjusting a scan repetition period according to a second method.

FIG. 12 is a flow chart illustrating an example of a method (second method) of adjusting the scan repetition period, and FIG. 13 illustrates a manner in which this process is performed. In this method, steps ST100 and ST111 at the end of the process are different from those of the process according to the first method described above with reference to the flow chart shown in FIG. 7. However, the other steps are similar to those of the first method.

In the first method described above, the scan repetition period $T_{SV}$ is adjusted by equally changing the pulse repetition period $T_P$. In the second method, in contrast to the first method, the pulse repetition period $T_P$ is changed only for some transmission pulses, and the pulse repetition period is maintained at the initial value for the other transmission pulses whereby the scan repetition period $T_{SV}$ is adjusted.

In the simplest case in the second method, of all transmission pulses in the scan repetition period $T_{SV}$, only the pulse period of the last transmission pulse is adjusted as the adjustment transmission pulse period $T_D$, and the initial value To is employed as the pulse repletion period for the other transmission pulses. The adjustment transmission pulse period $T_D$ is determined in step ST100 in FIG. 12.

This process is performed as shown in (c) and (d) of FIG. 13. From the scan repetition period $T_{SV}$ determined in step ST9, the adjustment transmission pulse period $T_D$ is calculated as $T_D = T_{SV} - T_{SVO} = T_{SV} - T_{PO} * N_B$, and this adjustment transmission pulse period $T_D$ is employed as the pulse period for the last transmission pulse.

Also in this second method, the requirement that the heartbeat period $T_{ECG}$ should be substantially equal to an integral multiple of the scan repetition period $T_{SV}$ is satisfied, and thus it is possible to minimize a useless period immediately before the ECG trigger signal.

(5) Adjusting of Scan Repetition Period (According to Third Method)

Figure 14:
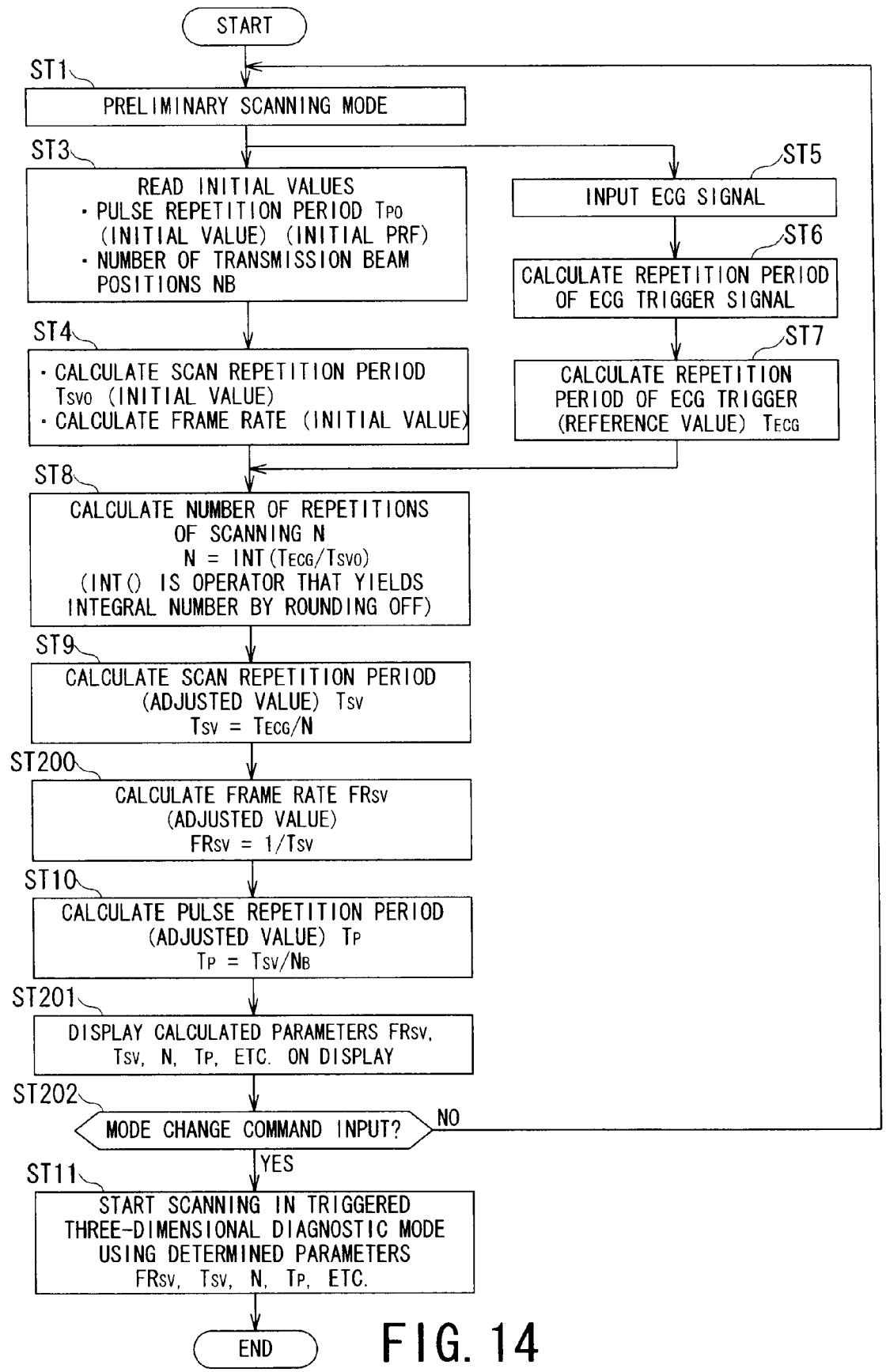
FIG. 14 is a flow chart illustrating an example of a method (third method) of adjusting a scan repetition period.

FIG. 14 is a flow chart illustrating an example of a method (third method) of adjusting the scan repetition period. In the first and second methods described above, when a mode change command is issued, the triggered three-dimensional diagnosis mode is automatically started based on the calculated diagnostic parameters (the scan repetition period $T_{SV}$, the pulse repetition period $T_P$, etc.).

In contrast, in the third method, the calculated diagnostic parameters are once displayed on the display unit 50 (step ST201) to allow a user to check the diagnostic parameters.

The user then inputs a command to change the operation into the triggered three-dimensional diagnosis mode via the operation unit 80. A determination as to whether the mode change command has been input is performed in step ST202.

The frame rate $FR_{SV}$ is one of important diagnostic parameters, and the process of this third method includes a step (ST200) in which the frame rate $FR_{SV}$ is calculated.

In the third method, because the operation enters the triggered three-dimensional diagnosis mode after the user checks the calculated diagnostic parameters, it is possible to perform diagnosis in a highly reliable manner.

In the ultrasonic diagnostic apparatus 1 and the method thereof according to the embodiments of the invention, as described above, it is possible to prevent the scanning operation from being aborted in a period immediately before the ECG trigger signal. Thus, an increase in the efficiency of using the acquired data is achieved, and it is possible to generate an image in the period immediately before the ECG trigger.

Note that the present invention is not limited to details of the embodiments described above, but many modifications are possible without departing from the spirit and scope of the present invention. Elements disclosed in the embodiments described above may be properly combined to embody the invention in various aspects. One or more elements may be removed from the configurations disclosed in the embodiments described above. Elements disclosed in different embodiments may be combined.

What is claimed is:

1. An ultrasonic diagnostic apparatus, comprising:
an ultrasonic probe configured to output a transmission pulse while scanning an ultrasonic beam in a main scanning direction and a sub scanning direction, and to detect a reflection signal from an inside of a body under examination;
a scan controller configured to input a trigger signal output every heartbeat period from an outside of the apparatus, to scan the ultrasonic beam such that a particular diagnostic region of the body under examination is scanned with the ultrasonic beam a plurality of times for a period from one trigger signal to a next trigger signal, and to control a scan repetition period by controlling a pulse repetition period of the transmission pulse; and
an image generation unit configured to generate an image corresponding to the scan repetition period,
the scan controller being configured to determine the pulse repetition period such that an integer multiple of the scan repetition period is equal to a reference value determined based on a period of the trigger signal, and to control the pulse repetition period according to the determination.

2. The ultrasonic diagnostic apparatus according to claim 1, wherein the scan controller is configured to scan the ultrasonic beam such that each of a predetermined number of blocks obtained by dividing the particular diagnostic region of the body under examination is scanned with the ultrasonic beam the plurality of times for the period from the one trigger signal to the next trigger signal, and to control the scan repetition period by controlling the pulse repetition period of the transmission pulse; and
the image generation unit is configured to generate an image of all of the diagnostic region by connecting data acquired as a result of repetitive scanning of each block in an order corresponding to an order in which the repetitive scanning is performed.

3. The ultrasonic diagnostic apparatus according to claim 1, wherein the scan controller is configured to determine the pulse repetition period such that the pulse repetition period is equally distributed over the scan repetition period, and to control the pulse repetition period according to the determination.

4. The ultrasonic diagnostic apparatus according to claim 3, wherein
the scan controller is configured to store an initial value of the pulse repetition period predetermined depending on a depth of the body under examination; and
the scan controller is configured to determine the pulse repetition period such that the pulse repetition period is longer than or equal to the initial value of the pulse repetition period.

5. The ultrasonic diagnostic apparatus according to claim 1, wherein
the scan controller is configured to store an initial value of the pulse repetition period predetermined depending on a depth of the body under examination; and
the scan controller is configured to determine the pulse repetition period such that, when an integer multiple of the scan repetition period determined based on the initial value of the pulse repetition period is not equal to the period of the trigger signal, an adjustment transmission pulse is provided in a part of the scan repetition period and a period of the adjustment transmission pulse is determined such that the integer multiple of the scan repetition period is equal to the period of the trigger signal.

6. The ultrasonic diagnostic apparatus according to claim 5, wherein the adjustment transmission pulse is a single transmission pulse disposed at the end of the scan repetition period.

7. The ultrasonic diagnostic apparatus according to claim 1, further comprising:
an operation unit configured to allow a user to operate to start controlling based on the determined pulse repetition period; and
a display unit configured to display one or more diagnostic parameters determined based on the determined pulse repetition period.

8. The ultrasonic diagnostic apparatus according to claim 7, wherein the one or more diagnostic parameters include at least one of the scan repetition period or a scan repetition rate; a number of repetitions of scanning; an area size of the diagnostic region; a depth of the diagnostic region; and a data acquisition disabled period.

9. A method of controlling an ultrasonic diagnostic apparatus, comprising:
(a) outputting a transmission pulse while scanning an ultrasonic beam in a main scanning direction and a sub scanning direction and detecting a reflection signal from an inside of a body under examination;
(b) inputting a trigger signal output every heartbeat period from an outside of the apparatus, scanning the ultrasonic beam such that a particular diagnostic region of the body under examination is scanned with the ultrasonic beam a plurality of times for a period from one trigger signal to a next trigger signal, and controlling a scan repetition period by controlling a pulse repetition period of the transmission pulse; and
(c) generating an image corresponding to the scan repetition period, wherein, in the step (b), the pulse repetition period is determined such that an integer multiple of the scan repetition period is equal to a reference value determined based on a period of the trigger signal, and the pulse repetition period is controlled according to the determination.

10. The method of controlling the ultrasonic diagnostic apparatus according to claim 9, wherein, in the step (b), each of a predetermined number of blocks obtained by dividing the particular diagnostic region of the body under examination is scanned with the ultrasonic beam the plurality of times for the period from the one trigger signal to the next trigger signal, and the scan repetition period is controlled by controlling the pulse repetition period of the transmission pulse; and
in the step (c), an image of all of the diagnostic region is generated by connecting data acquired as a result of repetitive scanning of each block in an order corresponding to an order in which the repetitive scanning is performed.

11. The method of controlling the ultrasonic diagnostic apparatus according to claim 9, wherein in the step (b), the pulse repetition period is determined such that the pulse repetition period is equally distributed over the scan repetition period, and the pulse repetition period is controlled according to the determination.

12. The method of controlling the ultrasonic diagnostic apparatus according to claim 11, wherein, in the step (b), an initial value of the pulse repetition period predetermined depending on a depth of the body under examination is stored, and the pulse repetition period is determined such that the pulse repetition period is longer than or equal to the initial value of the pulse repetition period.

13. The method of controlling the ultrasonic diagnostic apparatus according to claim 9, wherein in the step (b), an initial value of the pulse repetition period predetermined depending on a depth of the body under examination is stored, and the pulse repetition period is determined such that, when an integer multiple of the scan repetition period determined based on the initial value of the pulse repetition period is not equal to the period of the trigger signal, an adjustment transmission pulse is provided in a part of the scan repetition period and a period of the adjustment transmission pulse is determined such that the integer multiple of the scan repetition period is equal to the period of the trigger signal.

14. The method of controlling the ultrasonic diagnostic apparatus according to claim 13, wherein the adjustment transmission pulse is a single transmission pulse disposed at the end of the scan repetition period.

15. The method of controlling the ultrasonic diagnostic apparatus according to claim 9, further comprising:
in response to an operation performed by a user, starting controlling based on the determined pulse repetition period; and
displaying one or more diagnostic parameters determined based on the determined pulse repetition period.

16. The method of controlling the ultrasonic diagnostic apparatus according to claim 15, wherein the one or more diagnostic parameters include at least one of the scan repetition period or a scan repetition rate; a number of repetitions of scanning; an area size of the diagnostic region; a depth of the diagnostic region; and a data acquisition disabled period.

* * * * *